United States Patent

Adelberg

[11] 4,047,694
[45] Sept. 13, 1977

[54] CLAMP FOR REGULATING FLOW THROUGH PLASTIC-TUBING

[76] Inventor: Marvin Adelberg, 16821 Oak View Drive, Encino, Calif. 91436

[21] Appl. No.: 764,406

[22] Filed: Jan. 31, 1977

Related U.S. Application Data

[63] Continuation-in-part of Ser. No. 644,166, Dec. 24, 1975, Pat. No. 4,013,263.

[51] Int. Cl.² .............................................. F16K 7/06
[52] U.S. Cl. ........................................... 251/6; 251/7
[58] Field of Search ................................. 251/4, 6-10

[56] References Cited

U.S. PATENT DOCUMENTS

| | | | |
|---|---|---|---|
| 2,615,668 | 10/1952 | Ernest | 251/7 |
| 3,477,686 | 11/1969 | Engelsher et al. | 251/10 |
| 3,685,787 | 8/1972 | Adelberg | 251/6 |
| 3,802,463 | 4/1974 | Dabney | 251/6 X |
| 3,893,468 | 7/1975 | McPhee | 251/6 X |

FOREIGN PATENT DOCUMENTS

| 1,070,889 | 11/1954 | Germany | 251/8 |
|---|---|---|---|

Primary Examiner—William R. Cline
Assistant Examiner—Richard Gerard

[57] ABSTRACT

Tubing through which fluid flow is to be regulated is placed in a regulating clamp wherein it is clamped between a roller wheel and a surface having a variable cross-sectional area channel extending therealong. This surface is parallel to the travel path of the wheel, and thus there is a constant separation distance between these two elements for all wheel positions. Flow rate through the tubing is changed by longitudinal adjustment of the position of the roller wheel, the ratio of the portion of the tubing which is clamped between the wheel and the surface to that which is not clamped and over the channel thereby being varied. A plurality of ridge elements are formed in the surface and act to locally pinch or grip the tubing at discrete intervals, thereby substantially lessening creep of the plastic tubing. The edges of the roller wheel are undercut so as to form recessed shoulders which provides spaces into which the outer edges of the tubing can migrate, the width of the thus formed shoulders being sufficiently small so as to prevent the formation of a flow lumen in the edges of the tubing when the tubing is being clamped. Pinching action of the ridge elements combined with migration space provided by the recessed wheel shoulder portions for the edges of the tubing provide an improved minimization of flow rate change once the clamp has been set for the desired rate of flow. In addition, this combination of structure avoids increase in flow rate following a large tug on the tubing tending to cause the stretching thereof.

5 Claims, 5 Drawing Figures

CLAMP FOR REGULATING FLOW THROUGH PLASTIC-TUBING

This application is a continuation in part of my application Ser. No. 644,166, filed Dec. 24, 1975 and now Pat. No. 4,013,263.

This invention relates to clamp devices for use in regulating fluid flow through plastic tubing, and more particularly to such device utilizing a roller wheel which is longitudinally adjusted relative to a surface having a variable cross-section channel to adjust and set the flow rate in which the roller wheel has recessed shoulders formed along the edges thereof. In my application Ser. No. 644, 166, filed Dec. 24, 1975, an improved roller clamp device for use in regulating fluid flow through plastic tubing is described. This device employs means along the clamping surface of the clamp for pinching or gripping the tubing at discrete locations so as to confine small segments of the tubing between the pinching elements. This prior device has been found to significantly reduce the magnitude of creep of the plastic tubing, thereby providing a substantial improvement in the constancy of the fluid flow rate therethrough. It has been found, however, that while a substantially constant flow rate can be maintained under normal conditions, that if the plastic tubing is given a strong tug so as to cause a stretching of the relatively soft polyvinyl chloride tubing (generally Shore A 65-80), upon release a subsequent dramatic increase in flow rate occurs. Such a large uncontrolled increase in flow rate could present a serious hazard, particularly where potent drugs are being administered or where the patient is an infant or an elderly person. Such large increases in flow rate also can result in pulmonary edema (flooding of the lungs) which could be fatal.

The present invention provides a solution to the aforementioned problems which in one case are occasioned by accidental tugging of the plastic tubing in that it fully obviates any increase in flow rate with such tugging, there generally being, if any significant change in flow rate after such tugging, a decrease in the flow rate rather than an increase thereof. Further, it has been found that the device of the invention also provides a significant improvement over the device of my prior patent application in flow rate constancy.

It is therefore an object of this invention to prevent increases in flow rate in the administering of intravenous infusions subsequent to an inadvertent stretching of the intravenous feed line.

It is a further object of this invention to provide an improved clamp for regulating fluid flow through plastic tubing wherein creep of the tubing is lessened and increases in flow rate after strong tugs on the tubing are eliminated.

Other objects of this invention will become apparent as the description proceeds in connection with the accompanying drawings, of which:

Figure 1:
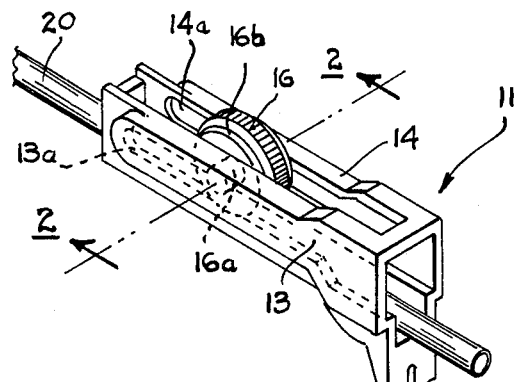
FIG. 1 is a perspective drawing of a preferred embodiment of the invention.
Figure 2:
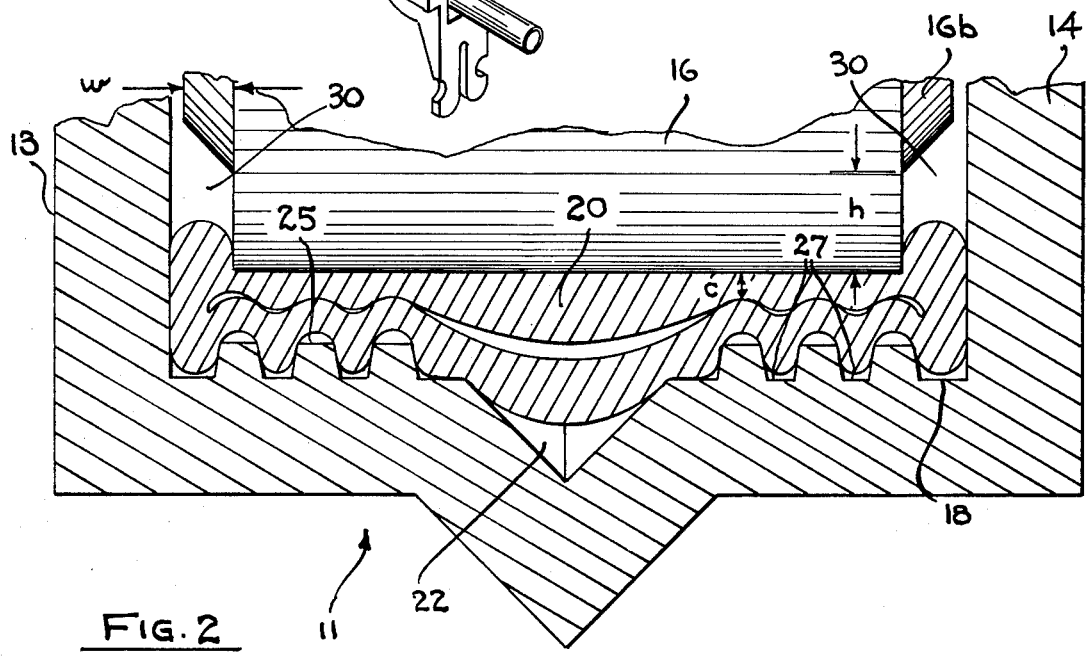
FIG. 2 is a portion of a cross-sectional view taken along the plane indicated by 2—2 in FIG. 1.
Figure 3:
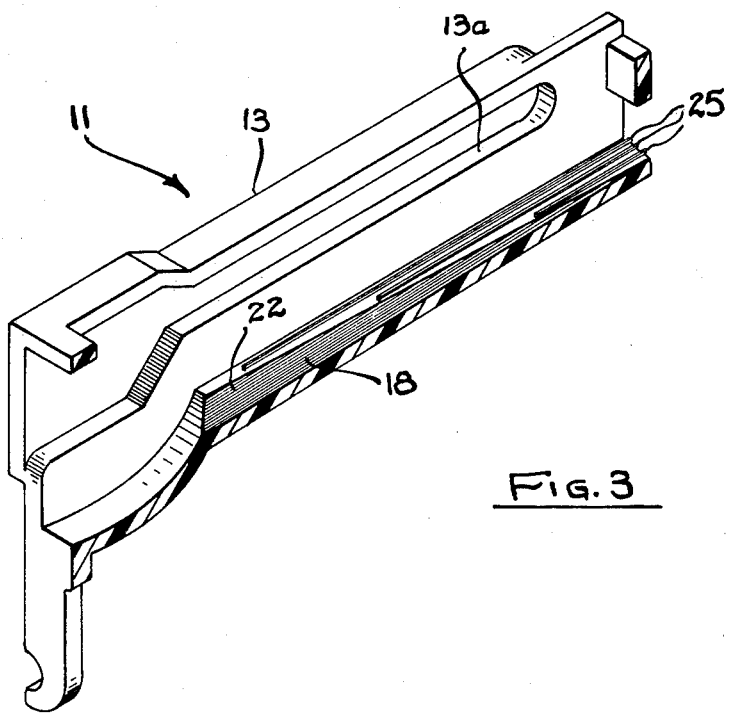
FIG. 3 is a perspective view with cut-away section of the body portion of the preferred embodiment.

Briefly described, the device of the invention is as follows: A flow regulating clamp of the type described in my aforementioned application No. 644,166, has a body portion with a longitudinal clamping surface. This clamping surface has a variable cross-section longitudinal channel formed therein. A roller wheel is mounted in the body for longitudinal motion parallel to the clamping surface, there being a constant clearance distance between the roller wheel and the clamping surface with motion of the wheel. Plastic tubing is clamped between the roller wheel and the clamping surface, the flow cross-sectional area of the tubing being adjusted in accordance with positioning of the wheel. The edges of the wheel are undercut to form stepped shoulders on opposite sides thereof. Recesses are thus formed between the sides of the wheel and the side walls of the body portion, into which the sides of the tubing can migrate with clamping and particularly immediately after a strong tug is exerted on the tubing. These recesses are large enough to permit adequate migration of the tubing so as to mitigate flow rate changes but not so large as to permit the formation of flow lumens in the sides of the tubing while the tubing is being clamped. This stepped shoulder structure has two advantages. First, it provides an improved minimization of the flow rate change under normal operation of the clamp. Secondly, in the event that the tubing should experience a strong tug, the marked increase in flow rate which occurs in prior art clamps is eliminated. It is to be noted that this improvement is only obtained with typical commercial intravenous tubing which has a Shore A index in the range 65-80, i.e., relatively soft. In the preferred embodiment, a plurality of raised portions which are separated from each other by discrete valley portions are formed in the clamping surface to locally pinch or grip the tubing at discrete locations or intervals, as described in my aforementioned patent application Ser. No. 644,166. The use of this structure substantially lessens the creep of the plastic and minimizes flow rate change once the clamp has been set for the desired rate of flow. The use of such gripping structure greatly localizes the tubing distortion when it is subjected to a tug. Any tubing distortion between the ridges or other gripping structure used will not propagate over to the large - groove region in the center of the housing where fluid flow is influenced. When pinched, some of the tubing sags slightly into the large - groove. On one side of the wheel, the - groove is wider and convergent in the direction toward the wheel. On the other side, the - groove is narrower and divergent in the direction towards the wheel. When the abusive tug is relaxed, the tubing on the convergent side recovers less completely because there is a tendency for the tubing to "bunch-up" and so to generate a slightly larger local lumen. On the other side of the wheel, the tubing tends to recover more easily because the groove is divergent toward the wheel. This effect, however, is overshadowed by the strongly localizing effect of the gripping elements. After the tug occurs, the side portions of the tube wall are permitted to migrate into the recesses formed between the undercut shoulder portions of the wheel and the sides of the housing. The tubing however remains sufficiently pinched in this area so as to permit no fluid flow in this section of the tube.

Figure 4:
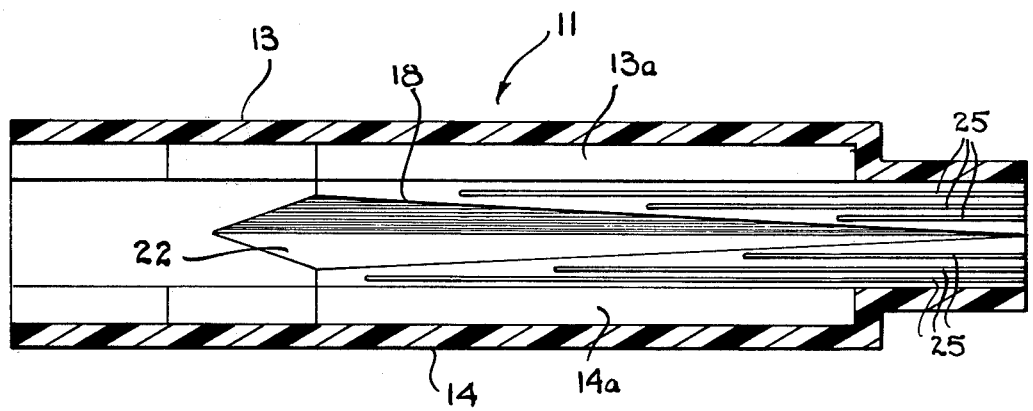
FIG. 4 is a cross-sectional view illustrating the clamping surface of the preferred embodiment.

Referring now to FIGS. 1-4, a preferred embodiment of the invention is illustrated. The clamp has a body portion or housing 11, having side walls 13 and 14 with oppositely positioned trunnion grooves 13a and 14a formed therein. Roller wheel 16 has a pair of trunnions (one of which 16a is shown in FIG. 1) extending therefrom which ride in grooves 13a and 14a respectively. The body portion also has a bottom surface 18 which serves as a clamping surface against which plastic tubing 20 is clamped by wheel 16. Formed in the central part of surface 18 is variable width and variable depth channel 22. Clamping surface 18 is parallel to grooves 13a and 14a such that the separation distance between wheel 16 and surface 18 remains constant throughout the travel of the wheel on its trunnions. The flow rate of fluid through tubing 20 is adjusted to the desired value by positioning wheel 16 along grooves 13a and 14a, whereby the tubing is compressed against surfaces which are adjacent to different portions of the channel which has varying depth and width. A plurality of ridges or raised portions 25 are formed in surface 18. Raised portions 25 are separated from each other by discrete valley portions 27. Ridges 25, as can best be seen in FIG. 4, are staggered relative to each other on opposite sides of channel 22. By staggering the ridges, the control obtained by moving the wheel is more continuous and monotonic than would be the case where the pattern is symmetrical. In the preferred embodiment, ridges 25 are made substantially parallel to the longitudinal axis of the body to facilitate manufacturing; however, they could also run in other directions and/or be a series of interrupted elements or ridges of equal or unequal length or height.

As explained in my aforementioned patent application, for minimum creep, the height of the ridges and the spacing between ridges are preferably made substantially equal to each other and to the compressed wall thickness of the tubing. Where polyvinyl chloride tubing having a shore hardness of Shore A 65–80 is used, the tubing wall when compressed against surface 18 by wheel 16 generally is reduced to a thickness of about one-half of its nominal uncompressed thickness. In an operative embodiment of the invention utilizing polyvinyl chloride tubing having a nominal wall thickness of 0.020 inches and an estimated compressed wall thickness of about 0.010 inches, ridges having a height and spacing of 0.006 inches were utilized.

The edges of wheel 16 are undercut to form recessed tapered shoulders 16b and recessed areas 30 between the sides of the wheel and the inner surfaces of wall 13 and 14. The edges of tubing 20 are thus permitted to migrate into recesses 30. The width "w" of the recessed area, and the length "h" thereof must be great enough to permit adequate migration of the tubing therein but at the same time must not be so great as to permit the formation of a flow lumen in this section of the tubing. It has been found that optimum results are achieved where the width "w" is twice the compressed wall thickness "c" of the tubing, where the height of the recess "h" (not considering the tapered portion of the shoulder) is at least twice "w". A greater dimension for "h" does not affect operation of the device except insofar as the structural factors of the wheel are concerned. The use of a sloped or tapered shoulder 16b rather than a 90° shoulder facilitates assembly but has no influence on the operation of the device.

Figure 5:
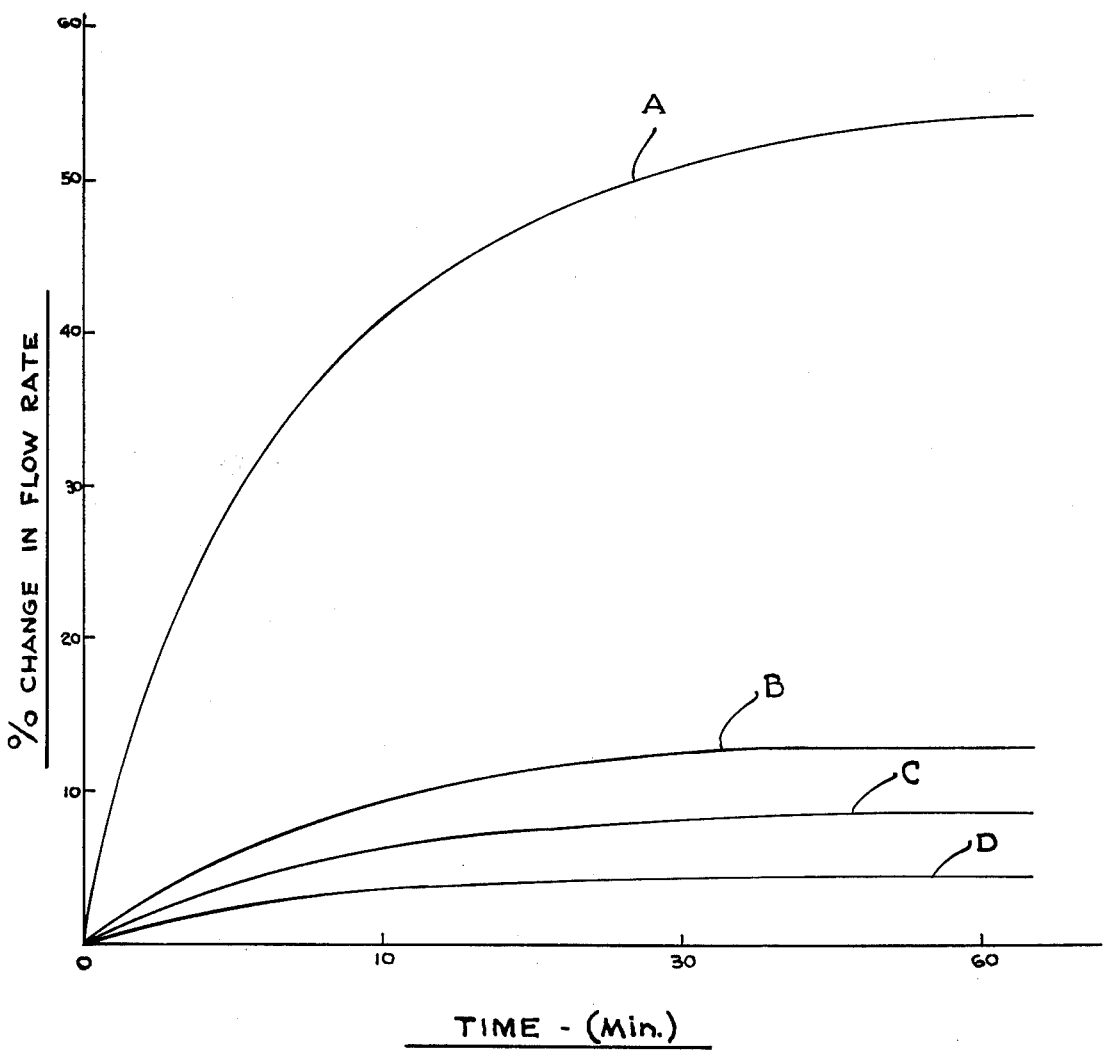
FIG. 5 is a graph illustrating some of the improved operations afforded by the device of the invention.

Referring now to FIG. 5, a graph is shown illustrating flow rate variations due to relative creep characteristics of conventional clamps, clamps made in accordance with my U.S. Pat. No. 3,685,787, clamps made in accordance with my patent application Ser. No. 644,166, and clamps made in accordance with the present invention. The graph line marked "A" indicates percentage change in flow rate in a prior art conventional clamp. The graph line marked "B" shows the percent change in flow rate with the clamp of my U.S. Pat. No. 3,685,787. The graph line marked "C" indicates the precent change in flow rate with the clamp of my patent application No. 644,166. The graph line marked "D" indicates the percent change in flow rate with the clamp of the present invention used with the same tubing as for graphs "A", "B" and "C", and having a nominal wall thickness of .020 inches (compressed wall thickness of 0.010 inches). In the case of graphs "C" and "D", the ridges had a height and spacing of 0.006 inches. It can be seen from this graph that the device of the present invention reduces the change in flow rate substantially as compared with the device of my application Ser. No. 644,166 and now U.S. Pat. No. 4,013,263.

While the invention has been described and illustrated in detail, it is to be clearly understood that this is intended by way of illustration and example only and is not to be taken by way of limitation, the spirit and scope of this invention being limited only by the terms of the following claims.

I claim:

1. In a clamp for regulating fluid flow through plastic tubing having a body portion with a longitudinal clamping surface, a variable cross-section longitudinal channel being formed in or along said surface, a roller wheel mounted in said body for longitudinal motion parallel to said clamping surface, and a plurality of distributed raised portions separated from each other by discrete valley portions formed in said clamping surface for locally gripping the tubing wall at given locations thereby restraining the tubing so as to reduce creep thereof, the tubing being clamped between the roller wheel and said surface, the improvement comprising:

undercut stepped shoulder portions formed in the opposite edges of said wheel defining recesses in the wheel edges, the width of each of said recesses being of the order of twice the compressed wall thickness of the tubing, the height of each of said recesses being at least twice the width thereof, whereby the side portions of the tubing are permitted to migrate into said recesses without forming a flow lumen in said side portions when the tubing is being clamped.

2. The clamp of claim 1 wherein said shoulder portions are tapered.

3. The clamp of claim 1 wherein the height of said raised portions above the lowest point of said valley portions and the separation between said raised portions have magnitudes of the order of the compressed wall thickness of the tubing.

4. The clamp of claim 3 wherein said raised portions are in the form of ridges which run substantially parallel to each other and to the longitudinal axis of the clamping surface.

5. The clamp of claim 4 wherein the ridges on one side of said channel are staggered with respect to the ridges on the other side of said channel.

* * * * *